United States Patent [19]

Phillipps et al.

[11] Patent Number: 4,578,221
[45] Date of Patent: Mar. 25, 1986

[54] ANDROSTANE CARBOTHIOIC ACIDS

[75] Inventors: Gordon H. Phillipps, Wembley; Brian M. Bain, Chalfont St. Peter; Stuart B. Laing, Harrow, all of England

[73] Assignee: Glaxo Group Limited, England

[21] Appl. No.: 513,396

[22] Filed: Jul. 14, 1983

Related U.S. Application Data

[63] Continuation of Ser. No. 408,837, Aug. 17, 1982, abandoned, which is a continuation of Ser. No. 256,845, Apr. 23, 1981, abandoned.

[30] Foreign Application Priority Data

Apr. 23, 1981 [GB] United Kingdom ............... 8013339

[51] Int. Cl.⁴ ............................................. C07J 3/00
[52] U.S. Cl. ................................................ 260/397.1
[58] Field of Search .................. 260/239.55 D, 397.1, 260/397.45

[56] References Cited

U.S. PATENT DOCUMENTS 3,697,558 10/1972 Bach et al. ............... 260/239.55 D
4,188,385 2/1980 Edwards ................... 260/239.55 D
4,263,289 4/1982 Edwards ..................... 260/397.1

Primary Examiner—Elbert L. Roberts
Attorney, Agent, or Firm—Bacon & Thomas

[57] ABSTRACT

Androstane carbothioic acids of the formula:

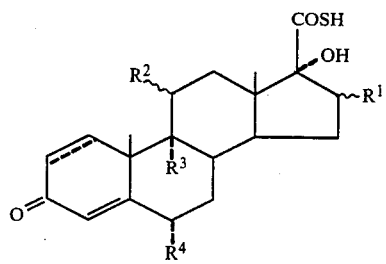

wherein
  $R^1$ represents a hydrogen atom, a hydroxy group in the α-configuration, a methyl group which may be in either the α- or β-configuration, or a methylene group;
  $R^2$ represents a hydroxy or protected hydroxy group in either the α- or β-configuration or an oxo group;
  $R^3$ represents a hydrogen, bromine, chlorine or fluorine atom; or $R^2$ and $R^3$ together represent a carbon-carbon bond or an epoxy group in the β-configuration;
  $R^4$ represents a hydrogen or fluorine atom; and the symbol represents a single or double bond and the salts thereof are useful as intermediates in the preparation of anti-inflammatory androstane 17β-carbothioate esters.

The compounds of formula I are prepared by reaction of a reactive derivative of a 17β-carboxylic acid corresponding to the compound of formula I with hydrogen sulphide or a sulphide or hydrosulphide salt.

8 Claims, No Drawings

ANDROSTANE CARBOTHIOIC ACIDS

This application is a continuation of application Ser. No. 408,837 filed Aug. 17, 1982 which is a continuation of Ser. No. 256,845 filed Apr. 23, 1981 both now abandoned.

BACKGROUND OF THE INVENTION

The present invention relates to androstane 17α-hydroxy-17β-carbothioic acids and to processes for the preparation thereof. The compounds of the invention are intermediates, primarily of use in preparing anti-inflammatory androstane 17β-carbothioate esters.

Anti-inflammatory steroids are most typically of the corticoid type, i.e. in the pregnane series. Certain androstane compounds containing a variety of carbothioate groupings in the 17β-position have been found to possess anti-inflammatory properties. In particular such androstane compounds are described and claimed in U.S. patent application Ser. No. 234,113 filed by G. H. Phillipps, B. M. Bain, C. Williamson, I. P. Steeples and S. B. Laing on Feb. 13, 1981.

In general, these anti-inflammatory androstane 17β-carbothioates have the partial formula

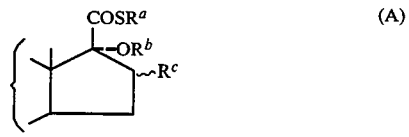

where $R^a$ represents a $C_{1-6}$ alkyl group, a $C_{1-2}$ alkyl group carrying a terminal halogen atom, or a benzyl group which may be substituted by a $C_{1-4}$ alkyl or $C_{1-4}$ alkoxy group or a halogen atom; and $OR^b$ represents a group —$OCOR^d$, where $R^d$ represents a hydrogen atom or a $C_{1-5}$ alkyl group and $R^c$ represents a hydrogen atom or a methyl group (in either the α- or β-configuration) or a methylene group or $OR^b$ and $R^c$ together represent a 16α,17α-isopropylidenedioxy group. They may be generally represented by the formula:-

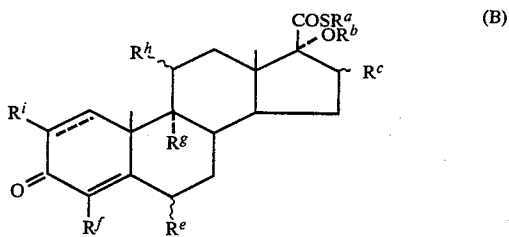

wherein $R^a$, $R^b$ and $R^c$ are as previously defined; $R^e$ represents a hydrogen, fluorine or chlorine atom in either the α- or β-configuration; $R^f$ represents a hydrogen, fluorine, chlorine or bromine atom; $R^g$ represents a hydrogen, fluorine, or chlorine atom; $R^h$ represents a hydroxy group in the β-configuration or a keto group or, when $R^g$ represents a chlorine atom, a chlorine or fluorine atom in the β-configuration; $R^i$ represents a hydrogen atom or where a 1,2-double bond is present, optionally a chlorine or bromine atom and the symbol ⁓ represents a single or double bond.

DESCRIPTION OF THE INVENTION

We have now discovered that 17α-hydroxy-17β-carbothioic acids, which have not hitherto been described, may readily be prepared and serve as useful intermediates, for example, in the preparation of such anti-inflammatory androstane compounds.

Thus according to one feature of the present invention we provide 17α-hydroxyandrostane 17β-carbothioic acids of the formula:-

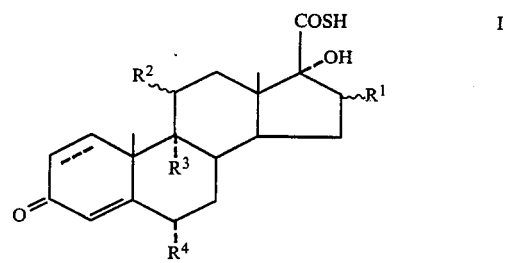

wherein
$R^1$ represents a hydrogen atom, a hydroxy group in the α-configuration, a methyl group which may be in either the α- or β-configuration, or a methylene group;
$R^2$ represents a hydroxy or protected hydroxy group in either the α- or β-configuration or an oxo group;
$R^3$ represents a hydrogen, bromine, chlorine or fluorine atom; or $R^2$ and $R^3$ together represent a carbon-carbon bond or an epoxy group in the β-configuration;
$R^4$ represents a hydrogen or fluorine atom; and the symbol ⁓ represents a single or double bond and the salts thereof.

Compounds of formula (I) and salts thereof which are particularly useful intermediates for preparing androstane 17β-carbothioates include those in which $R^1$ represents a hydrogen atom, an α- or β-methyl group or a methylene group.

Preferred compounds of formula I and salts thereof by virtue of their utility as intermediates for preparing androstane 17β-carbothioates with high anti-inflammatory activity, include those compounds in which $R^1$ represents a methyl group in the α- or β-configuration or a methylene group; $R^3$ represents a fluorine atom; $R^4$ represents a hydrogen atom or a fluorine atom, $R^2$ represents a hydroxy group in the β-configuration or an oxo group, and the symbol ⁓ in the 1,2-position represents a carbon-carbon double bond; and salts thereof.

Especially preferred compounds of formula I thus include, for example, the following:

9α-Fluoro-11β,17α-dihydroxy-16β-methyl-3-oxoandrosta-1,4-diene-17β-carbothioic acid and the salts thereof;

9α-Fluoro-17α-hydroxy-16β-methyl-3,11-dioxoandrosta-1,4-diene-17β-carbothioic acid and the salts thereof;

9α-Fluoro-11β,17α-dihydroxy-16α-methyl-3-oxoandrosta-1,4-diene-17β-carbothioic acid and the salts thereof;

9α-Fluoro-17α-hydroxy-16α-methyl-3,11-dioxoandrosta-1,4-diene-17β-carbothioic acid and the salts thereof;

9α-Fluoro-11β,17α-dihydroxy-16-methylene-3-oxoandrosta-1,4-diene-17β-carbothioic acid and the salts thereof;

9α-Fluoro-17α-hydroxy-16-methylene-3,11-dioxoandrosta-1,4-diene-17β-carbothioic acid and the salts thereof;

6α,9α-Difluoro-11β,17α-dihydroxy-16α-methyl-3-oxoandrosta-1,4-diene-17β-carbothioic acid and the salts thereof; and 6α,9α-Difluoro-17α-hydroxy-16α-methyl-3,11-dioxoandrosta-1,4-diene-17β-carbothioic acid and the salts thereof.

Protected hydroxy groups at the 11-position include for example trialkylsilyloxy e.g. trimethylsilyloxy groups or perfluoro or chloroalkanoyloxy e.g. trifluoroacetoxy groups.

Salts of the carbothioic acids of formula I include, for example alkali metal, e.g. lithium, sodium or potassium salts; alkaline earth metal e.g. calcium or magnesium salts; tertiary amine salts, e.g. pyridinium or triethylammonium salts; or quaternary ammonium salts, e.g. tetrabutyl ammonium salts.

The above mentioned 17β-carbothioic acids and their salts may, for example, be prepared by reaction of a reactive derivative of a 17β-carboxylic acid having the formula

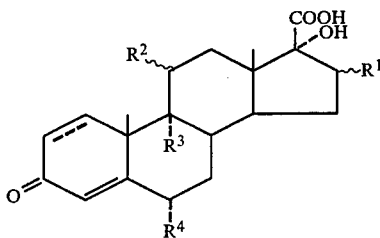

II (wherein) $R^1$, $R^2$, $R^3$ and $R^4$ are as herein defined) with hydrogen sulphide or a sulphide or hydrosulphide salt. Where a salt is used, the product having the formula I will be in salt form. In general, the cation of the sulphide or hydrosulphide salt may be as described above in relation to compounds of formula I, for example an alkali metal salt such as sodium or potassium hydrogen sulphide. The above-mentioned reactive derivative is preferably a 17α-hydroxy-androstane represented by the formula

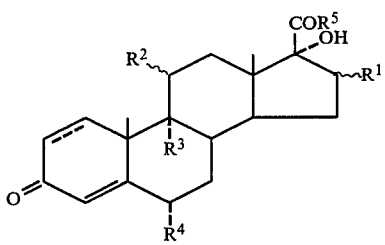

III (wherein $R^1$, $R^2$, $R^3$ and $R^4$ are as herein defined and $R^5$ represents a group of the formula

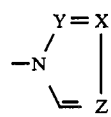

in which X, Y and Z, which may be the same or different, each represents CH or N, one or two of X, Y and Z being N, the heterocyclic ring optionally being substituted on at least one carbon atom by a lower alkyl group (e.g. with 1 to 4 carbon atoms, such as a methyl group) and/or where the heterocyclic ring contains two adjacent carbon atoms, the said ring optionally carrying a benzene ring fused to the said adjacent carbon atoms).

The reactive derivatives of formula III are preferably prepared by reacting the carboxylic acid of formula II with a symmetric or asymmetric compound of the formula:

$$R^5-W-R^5 \qquad IV$$

wherein W represents the group CO, CS, SO or $SO_2$ and the groups $R^5$, which may be the same or different, have the above meanings.

The compounds of formula IV are conveniently symmetric. In general, compounds of formula IV in which W represents CO, CS or SO will be used. Thus, for example, especially useful compounds of formula IV include N,N'-carbonyldi(1,2,4-triazole), N,N'-carbonyldibenzotriazole, N,N'-carbonyldibenzimidazole, N,N'-carbonyldi(3,5-dimethylpyrazole), N,N'-thionyldiimidazole and especially N,N'-carbonyldiimidazole and N,N'-thiocarbonyldiimidazole.

The preparation of a compound having the formula I as herein defined is conveniently effected by reaction of a carboxylic acid having the formula II with a compound of formula IV followed by reaction of the intermediate product having the formula III thereby obtained with hydrogen sulphide or a salt thereof preferably in situ without isolation of the intermediate.

The reaction with the compound of formula IV is conveniently effected in the presence of an inert anhydrous solvent e.g. a substituted amide solvent such as N,N-dimethylformamide or N,N-dimethylacetamide, desirably in the absence of water, advantageously at or below ambient temperature e.g. at a temperature of from −30° C. to +30° C. The reaction is conveniently effected under approximately neutral conditions, advantageously in an inert atmosphere, e.g. under nitrogen. The same solvents and conditions are also applicable to the subsequent reaction with $H_2S$ or a salt thereof. The heterocyclic compound e.g. imidazole or 1,2,4-triazole formed as a by-product may, for example, be readily removed by extraction with dilute acid.

In the starting 17α-hydroxy-17β-carboxylic acids having the formula II the 16-position will conveniently be substituted by the $R^1$ grouping desired in the final product. They may be prepared in conventional manner, e.g. by oxidation of an appropriate 21-hydroxy-20-keto pregnane.

The oxidative removal of the 21-carbon atom of the pregnane starting material may be effected for example with periodic acid, in a solvent medium and preferably at room temperature. Alternatively, sodium bismuthate may be employed to effect the desired oxidative removal of the 21-carbon atom of a 17α-acyloxy pregnane compound, followed by hydrolysis to the corresponding 17α-hydroxy compound.

As will be appreciated should the starting pregnane compound contain any substituent sensitive to the above described oxidation, such a group should be suitably protected.

As stated above the compounds of formula I are intermediates useful in the production of 17β-carbothioate esters and thus according to a further feature of the present invention there is provided a process for preparing an androstane 17α-hydroxy-17β-carbothioate represented by the formula

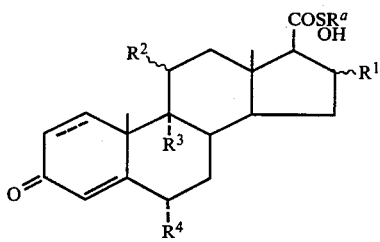

(wherein $R^1$, $R^2$, $R^3$ and $R^4$ are as herein defined and $R^a$ represents a $C_{1-6}$ alkyl group, or $C_{1-2}$ alkyl group carrying a terminal halogen atom or a benzyl group which may be substituted by a $C_{1-4}$ alkyl or $C_{1-4}$ alkoxy group or a halogen atom and the symbol ═══ represents a single or double bond which comprises esterifying the 17β-carbothioic acid group of an androstane of formula I or a salt thereof. Any other reactive groups present in the molecule may be suitably protected as desired.

Thus for example, in order to prepare a S-methyl or S-ethyl ester the 17β-carbothioic acid may be reacted with an appropriate diazoalkane, e.g. diazomethane, the reaction being preferably effected in a solvent medium, e.g. ether, tetrahydrofuran or methanol, and at a low temperature, preferably at $-5°$ to $+30°$ C. More preferably, a salt of the parent 17β-carbothioic acid for example, an alkali metal, e.g. lithium, sodium or potassium, salt or an alkylammonium, e.g. triethylammonium or tetrabutylammonium, salt may be reacted with an appropriate alkylating or aralkylating agent, preferably in a polar solvent such as a ketone, e.g. acetone or an amide such as dimethylformamide, dimethylacetamide or hexamethylphosphoramide, conveniently at a temperature of 15° to 100° C. For example, for the preparation of an S-alkyl such as a S-methyl or S-ethyl or S-aralkyl such as S-benzyl 17β-carbothioate, the alkylating or benzylating agent may comprise an alkyl or benzyl halide e.g. the iodide or bromide, or a dialkyl sulphate e.g. dimethylsulphate, or an O-alkyl-N,N'-dicyclohexylisourea. For the preparation of compounds in which $R^a$ represents a haloalkyl group, the alkylating agent may comprise an appropriate dihalo compound i.e. one containing a further halogen atom (preferably a bromine or iodine atom) in addition to the halogen atom of the desired $R^a$ group. This process is particularly applicable to the preparation of compounds in which $R^a$ is a chloromethyl group, the alkylating agent advantageously being bromochloromethane.

The esterification (i.e. the introduction of $R^a$ into a compound of formula I) may also be effected in a multistage process, especially where $R^a$ represents a haloalkyl group. Thus, for example, the COSH group of the 17α-hydroxy-17β-carbothioic acid of formula I especially in salt form, may be converted to the group $-COS(CH_2)_nY$ (wherein Y represents a displaceable substituent and n is 1 or 2) at the 17β-position, for example by conversion of the said acid or salt thereof to the corresponding hydroxyethyl thioester, e.g. with a halohydrin such as 2-iodoethanol, followed by substitution of the hydroxy group in the 2'-hydroxyethyl group by Y. Y may for example represent an alkyl- or aryl-sulphonyloxy group e.g. a mesyloxy or tosyloxy group.

A 2'-haloethyl 17β-carbothioate compound of formula V may then be prepared for example from a corresponding compound of formula I having as 17β-substituent the group $-COS(CH_2)_nY$ (wherein n=2 and Y is as hereinbefore defined) by reaction with an appropriate alkali metal, alkaline earth metal or quaternary ammonium halide, e.g. lithium chloride, conveniently in a solvent medium, e.g. acetone, dimethylformamide, hexamethylphosphoramide or ethanol.

Fluoromethyl or 2'-fluoroethyl-17β-carbothioate compounds of formula (I) may also be prepared from the corresponding chloro or more preferably bromo or iodo compounds by reaction with an appropriate fluoride, e.g. silver monofluoride or silver difluoride, conveniently in a solvent, for example acetonitrile.

It will be appreciated that one advantage of the compounds of the invention as intermediates in the preparation of products having formula (B) is that they permit the formation of 17β-carbothioates when the corresponding thiols are not conveniently available.

The active final products into which the intermediates having the formula I may be converted generally possess a 17α-acyloxy or 16α,17α-acetonide grouping and thus according to a still further feature of the present invention there is provided a process for the preparation of androstane 17β-carbothioic acids and salts thereof represented by the formula:-

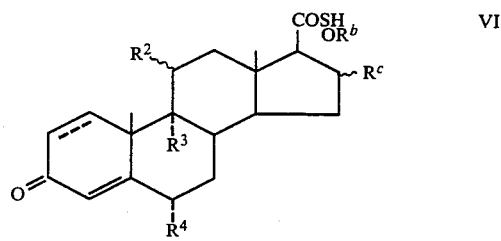

(wherein $R^2$, $R^3$ and $R^4$ are as herein defined; $OR^b$ represents a group $-OCOR^d$ where $R^d$ represents a hydrogen atom or a $C_{1-5}$ alkyl group; and $R^c$ is as defined for $R^1$; or $OR^b$ and $R^c$ together represent a 16α,17α-isopropylidenedioxy group and the symbol ═══ represents a single or double bond), which process comprises esterifying the 17α-hydroxy group of an androstane having the formula I or reaction with acetone to convert the 16α,17α-diol grouping, where present, to the 16α,17α-acetonide grouping. Any other reactive groups present in the molecule may be suitably protected as desired.

The esterification of the 17α-hydroxy group may, if desired, be effected by conventional techniques, e.g. by reacting the parent 17α-hydroxy compound with a mixed anhydride of the required carboxylic acid, which may, for example, be generated in situ by reacting the carboxylic acid with an appropriate anhydride such as trifluoroacetic anhydride, preferably in the presence of an acid catalyst, e.g. p-toluenesulphonic acid or sulphosalicylic acid. Alternatively, the mixed anhydride may be generated in situ by reaction of a symmetrical anhydride of the required acid with an appropriate further acid, e.g. trifluoroacetic acid.

The reaction is advantageously effected in an organic solvent medium such as benzene, methylene chloride or an excess of the carboxylic acid employed, the reaction being conveniently effected at a temperature of 20°–100° C.

Alternatively, the 17α-hydroxy group may be esterified by reaction of the parent 17α-hydroxy compound with the appropriate acid anhydride or acid chloride, if desired, in the presence of non-hydroxylic solvents, e.g. chloroform, methylene chloride or benzene, and preferably in the presence of a strong acid catalyst, e.g. perchloric acid, p-toluenesulphonic acid or a strongly acidic cation exchange resin, e.g. Amberlite IR 120, the reaction being conveniently effected at a temperature of 25° to 100° C.

The esterification of the 17α-hydroxy group may, if desired be effected by reacting the parent 17α-hydroxy-17β-carbothioic acid with the appropriate carboxylic acid chloride, preferably in a solvent such as a halogenated hydrocarbon e.g. dichloromethane, and advantageously in the presence of a base such as triethylamine, preferably at a low temperature e.g. 0° C.

Where a compound having the formula I is used in which $R^1$ represents an o-hydroxy group, the corresponding 16α,17α-acetonide 17β-carbothioic acid may conveniently be prepared by reaction of the 16α,17α-dihydroxy-17β-carbothioic acid with acetone in the presence of a strong acid e.g. toluene p-sulphonic acid.

The foregoing reactions may also be carried out on compounds having a variety of substituents or groupings which are subsequently converted into those present in the compounds of formulae I, V or VI as defined above.

Those compounds of formulae I, V or VI having an 11β-hydroxy group may thus be prepared by reduction of a corresponding 11-oxo compound, e.g. using an alkali metal or alkaline earth metal borohydride, e.g. sodium or calcium borohydride, conveniently in an alcoholic or aqueous alcoholic solvent such as methanol or ethanol.

Such an 11-keto compound may be prepared by oxidation of a corresponding 11α-hydroxysteroid, for example using a chromic acid reagent such as Jones' reagent.

An 11β-hydroxy compound of formula II may also be obtained by deprotection of a corresponding compound having a protected hydroxy group at the 11β-position, for example a trialkylsilyloxy group such as the trimethylsilyloxy group or a perfluoroalkanoyl group such as the trifluoroacetyl group. The alkyl groups in such a trialkylsilyloxy group preferably each contain 1–6 carbon atoms. Removal of the protecting group may be effected by hydrolysis, the trialkylsilyl group, being readily removed by mild acid or basic hydrolysis or particularly conveniently using a fluoride e.g. hydrogen fluoride or an ammonium fluoride. The perfluoro- or chloro-alkanoyl protecting group may also be removed by mild acid or basic hydrolysis, but preferably under acidic conditions when there is a 9α-chlorine atom. Such a protected hydroxyl group may be introduced, for example, by reacting a 11β-hydroxy steroid with an appropriate reagent such as a trialkylsilyl halide or a perfluoro- or chloro-alkanoic anhydride.

Compounds of formulae I, V or VI having a 3-keto group may be obtained by deprotection of a corresponding compound having a protected keto group at the 3-position, for example an enol ether or ester grouping. Such a grouping may be deprotected by, for example, hydrolysis e.g. acid hydrolysis. An enol ether or ester grouping may be introduced by, for example, known techniques such as reaction of the 3-ketone with an etherifying or esterifying reagent under enolising conditions.

Compounds of formulae I, V or VI having a 9α-halogen atom and an 11β-hydroxyl group may also be produced by reaction of a corresponding compound having a 9,11-double bond (and no substituent in the 11-position) with reagents serving to introduce the required 9α-halo-11β-hydroxy grouping. This may involve initial formation of a bromohydrin by reaction with an N-bromo-amide or -imide such as N-bromosuccinimide, followed by formation of the corresponding 9β,11β-epoxide by treatment with a base and reaction of the epoxide with hydrogen fluoride or hydrogen chloride to introduce the required fluorohydrin or chlorohydrin grouping respectively. Alternatively, the 9,11-olefin compound may be reacted with an N-chloro-amide or -imide to introduce the required 9α-chloro-11β-hydroxy grouping directly.

Compounds of formulae I, V or VI having a 4,5-double bond can conveniently be prepared by partial reduction of the corresponding $\Delta^{1,4}$-compound, for example, by hydrogenation using a palladium catalyst, conveniently in a solvent e.g. ethyl acetate or by homogeneous hydrogenation using for example tris(triphenylphosphine)rhodium chloride, conveniently in a solvent such as benzene, or by exchange-hydrogenation using for example cyclohexene in the presence of a palladium catalyst in a solvent e.g. ethanol, preferably under reflux. This reduction may be carried out on a haloalkyl ester where this is sufficiently stable in such a reaction or may be effected at an earlier stage.

Compounds of formula I, V or VI having a fluorine atom in the 6-position can also be prepared, from the corresponding 3-enol ester or ether followed by reaction with an electrophilic fluorinating agent such as perchloryl-fluoride and subsequent hydrolysis to yield the corresponding 6β-fluoro compound. Where no 1,2-double bond is present, treatment with a strong acid such as hydrogen chloride or more preferably hydrogen bromide effects epimerisation to form the 6α-fluoro compound. The epimerisation is preferably effected in a non-aqueous solvent medium, dioxan being particularly preferred; other solvents which may be used include tetrahydrofuran, ester solvents such as ethyl acetate, ketone solvents and amide solvents such as dimethylacetamide or dimethylformamide. The epimerisation is also advantageously effected in the presence of a carboxylic acid such as acetic acid, especially when hydrogen bromide is employed. In the case of $\Delta^{1,4}$-compounds, such epimerisation is sometimes difficult and it is preferable to hydrogenate the 1,2-double bond, e.g. by catalytic hydrogenation, effect the epimerisation and re-introduce the 1,2-double bond by dehydrogenation, normally under neutral or mildly acidic conditions e.g. using dichloro-dicyanoquinone or chloranil.

Where it is desired to prepare an anti-inflammatory compound having an 11β-hydroxy group it may be convenient to effect the necessary reactions on the corresponding 11-keto compound, the 11-ketone compound being converted to the corresponding 11β-hydroxy group as the last stage in the reaction sequence.

It will be appreciated that the above-mentioned anti-inflammatory compounds of formula (A) may, be readily prepared from corresponding compounds of formula V by esterification of the free 17α-hydroxy group, or from corresponding compounds of formula VI by esterification of the free 17β-carbothioic acid group or a salt thereof. The esterification of the free 17α-hydroxy group in the compounds of formula V may, for example, be effected as described in relation to the esterification of the free 17α-hydroxy group in the compounds of formula I. Similarly the esterification of the free 17β-carbothioic acid group or a salt thereof in the compounds of formula VI may, for example, be effected as described in relation to the esterification of the free 17β-carbothioic acid group or a salt thereof in the compounds of formula I.

9α-Fluoro-17α-hydroxy-16β-methyl-3,11-dioxoandrosta-1,4-diene-17β-carboxylic acid is believed to be a novel compound and thus constitutes a still further feature of the present invention. This novel compound may for example be prepared by oxidative removal of the 21-carbon atom from 9α-fluoro-17,21-dihydroxy-16β-methylandrosta-1,4-diene-3,11,20-trione according to conventional techniques e.g. by reaction with periodic acid, conveniently in a solvent medium e.g. tetrahydrofuran and preferably at about ambient temperature e.g. from 0° to 30° C.

The following Examples illustrate the present invention.

Melting points were determined in °C. on a Kofler block and are uncorrected. Optical rotations were determined at room temperature and solutions were dried over magnesium sulphate unless otherwise stated.

EXAMPLE 1

9α-Fluoro-11β,17α-dihydroxy-16β-methyl-3-oxoandrosta-1,4-diene-17β-carbothioic Acid A stirred solution of 9α-fluoro-11β,17α-dihydroxy-16β-methyl-3-oxoandrosta-1,4-diene-17β-carboxylic acid (0.502 g) in dry N,N-dimethylformamide (15 ml) was cooled at −5° under nitrogen and treated with N,N'-carbonyldiimidazole (0.435 g) and the reaction was stirred at −5° for 18 hrs. Hydrogen sulphide gas was bubbled into the reaction for 20 min and the solution was stirred for a further 4 hrs, gradually being allowed to warm to 22°. The reaction was poured into ethyl acetate and the resulting solution was washed with 2N-hydrochloric acid and water, then extracted with 2N-sodium carbonate solution (3×50 ml). The combined extracts were washed with ethyl acetate (60 ml) then covered with further ethyl acetate (100 ml) and acidified with hydrochloric acid to pH 1.0. The aqueous layer was extracted with further ethyl acetate and the extracts were washed with water and saturated sodium chloride solution, then dried and the solvent was removed in vacuo to give a white solid which was crystallised twice from ethyl acetate to give the title carbothioic acid (0.315 g) m.p. 198° to 201° (dec), $[\alpha]_D + 189°$ (c 0.71, dioxan).

EXAMPLE 2

9α-Fluoro-17β-hydroxy-16β-methyl-3,11-dioxoandrosta-1,4-diene-17β-carbothioic Acid A stirred solution of 9α-fluoro-17α-hydroxy-16β-methyl-3,11-dioxoandrosta-1,4-diene-17β-carboxylic acid (5.587 g) in dry N,N-dimethylformamide (150 ml) at 20° under nitrogen was treated with N,N'-carbonyldiimidazole (4.847 g) and the reaction was stirred at 20° for 4 hrs. Hydrogen sulphide gas was bubbled into the reaction for 10 min and the solution was stirred for a further hour. The solution was poured onto ice (300 ml) and 2N-hydrochloric acid (100 ml) to give a buff precipitate. This was filtered off, air dried overnight (6.268 g) and crystallised from ethyl acetate to give the title carbothioic acid (3.761 g) as white prisms, m.p. 215 to 218°, $[\alpha]_D + 143°$ [c 0.88, dimethylformamide]

EXAMPLE 3

9α-Fluoro-17α-hydroxy-16β-methyl-3,11-dioxoandrosta-1,4-diene-17β-carbothioic Acid A stirred solution of 9α-fluoro-17α-hydroxy-16β-methyl-3,11-dioxoandrosta-1,4-diene-17β-carboxylic acid (1.059 g) in dry N,N-dimethylformamide (50 ml) at 20° under nitrogen was treated with N,N'-thiocarbonyldiimidazole (1.368 g) and the reaction was stirred at 20° for 4 hrs. Hydrogen sulphide gas was bubbled into the reaction for 5 min. and the solution was stirred for a further hour. The reaction was partitioned between ethyl acetate (100 ml) and 2N-hydrochloric acid (100 ml) and the organic phase was washed with 2N-hydrochloric acid (100 ml) and water (2×100 ml) and was extracted with 2N-sodium carbonate solution (2×75 ml). The combined extracts were washed with ethyl acetate (50 ml), then covered with ethyl acetate (100 ml) and acidified with hydrochloric acid to pH1. The aqueous layer was extracted with further ethyl acetate (50 ml) and the combined extracts were washed with water (3×), saturated sodium chloride solution, dried, and the solvent was removed in vacuo. The residue was crystallied from ethyl acetate to give the title carbothioic acid (0.559), m.p. 212° to 219°, $[\alpha]_D + 145°$ [c 0.81, dimethylformamide]

EXAMPLE 4

S-Chloromethyl 9α-fluoro-11β,17α-dihydroxy-16β-methyl-3-oxoandrosta-1,4-diene-17β-carbothioate A stirred solution of 9α-fluoro-11β,17α-dihydroxy-16β-methyl-3-oxoandrosta-1,4-diene-17β-carbothioic and (0.169 g) and sodium hydrogen carbonate (0.040 g) in N,N-dimethylformamide (6 ml) was treated with bromochloromethane (0.1 ml) and stirring was continued at 22° for 1 hr. The reaction mixture was diluted with ethyl acetate (100 ml) and the solution was successively washed with 2N-hydrochloric acid (2×), water (2×), 2N-sodium carbonate solution (2×), water (2×) and saturated sodium chloride solution, then dried (MgSO4) and the solvent was removed in vacuo. The residue was crystallised twice from ethyl acetate to give the title S-chloromethyl thiolester (0.193 g) as white plates solvated with ethyl acetate (1 mol), m.p. 126° to 130°, $[\alpha]_D + 147.5°$ (c 0.64, dioxan).

EXAMPLE 5

9α-Fluoro-16β-methyl-3,11-dioxo-17α-propionyloxyandrosta-1,4-diene-17β-carbothioic Acid A stirred solution of 9α-fluoro-17α-hydroxy-16β-methyl-3,11-dioxoandrosta-1,4-diene-17β-carbothioic acid (0.485 g) and triethylamine (0.57 ml) in dichloromethane was cooled in ice-salt, treated with propionyl chloride (0.43 ml) and the reaction was stirred at 0° for 1.5 hr. The mixture was partitioned between ethyl acetate (75 ml) and 2N-sodium carbonate solution (75 ml) and the organic layer was successively used with further 2N-sodium carbonate solution, water (2×), 2N-hydrochloric acid, water (2×), and saturated sodium chloride solution, then dried and the solvent removed in vacuo to give a yellow crystalline solid (0.562 g). This was dissolved in acetone (10 ml), diethylamine (1.0 ml) was added and the reaction was stirred at 22° for 1.25 hr. The solvents were removed in vacuo and the residue was partitioned between ethyl acetate (30 ml) and 2N- hydrochloric acid (30 ml). The ethyl acetate layer was washed with water (2×) and extracted with 2N-sodium carbonate solution (2×30 ml). The combined extracts were washed with ethyl acetate (30 ml) and covered with ethyl acetate (60 ml) and acidified to pH 1.0 with hydrochloric acid. The ethyl acetate layer was washed with water (3×) and saturated sodium chloride solution, then dried (MgSO$_4$) and the solvent was removed in vacuo to give a white solid which was crystallised twice from ethyl acetate to give the title ester (0.290 g), m.p. 173° to 180°, $[\alpha]_D+148°$ (c 1.03, dioxan).

EXAMPLE 6

S-Chloromethyl
9α-fluoro-17α-hydroxy-16β-methyl-3,11-dioxoandrosta-1,4-diene-17β-carbothioate A solution of 9α-fluoro-17α-hydroxy-16β-methyl-3,11-dioxoandrosta-1,4-diene-17β-carbothioic acid (5.006 g), and sodium bicarbonate (1.612 g) in N,N-dimethylacetamide (50 ml) was treated with bromochloromethane (1.24 ml) and the reaction was stirred at 22° for 3.3 hrs. The solution was diluted with ethyl acetate (70 ml) and washed successively with 2N-hydrochloric acid, water, sodium metabisulphite solution, water (3×) and saturated sodium chloride solution, then dried and the solvent was removed in vacuo to give a cream solid (3.638 g). The analytical sample was obtained after preparative t.l.c. (silica gel, developed with chloroform:acetone=9.1), and crystallised from ethyl acetate as colourless prisms of the title ester (0.262 g), m.p. 223° to 228°, $[\alpha]_D+251°$ (c 1.2, dioxan).

EXAMPLE 7

S-Methyl
9α-Fluoro-17α-hydroxy-16β-methyl-3,11-dioxoandrosta-1,4-diene-17β-carbothioate A solution of 9α-fluoro-17α-hydroxy-16β-methyl-3,11-dioxoandrosta-1,4-diene-17β-carbothioic acid (1.009 g) and sodium hydrogen carbonate (0.458 g) in N,N-dimethylacetamide (10 ml) was treated with iodomethane (0.24 ml). The clear solution was stirred at 22° for 37 min. then partitioned between ethyl acetate (50 ml) and 2N-hydrochloric acid (50 ml). The organic layer was successively washed with water, saturated sodium hydrogen carbonate solution, water (3×) and saturated sodium chloride solution, then dried and the solvent was removed in vacuo to give a white solid which was crystallised from ethyl acetate to give the title methyl thioester (0.492 g) as white plates, m.p. 242° to 248°, $[\alpha]_D+193°$ (c 0.76, dioxan).

EXAMPLE 8

9α-Fluoro-11β-hydroxy-16β-methyl-3-oxo-17α-propionyloxyandrosta-1,4-diene-17β-carbothioic Acid.

A stirred solution of 9α-fluoro-11β,17α-dihydroxy-16β-methyl-3-oxoandrosta-1,4-diene-17β-carbothioic acid (0.511 g)in dichloromethane (20 ml) containing triethylamine (0.6 ml) was cooled to 2° and treated with propionyl chloride (0.45 ml) and the reaction was stirred at 2° for 2.5 hrs. The reaction was partitioned between ethyl acetate and sodium hydrogen carbonate and the organic phase was washed with water, 2N-hydrochloric acid, water and saturated sodium chloride solution, dried and the solvent removed in vacuo to give a colourless solid (0.634 g).

This was dissolved in acetone (30 ml), diethylamine (1.5 ml) added and the clear solution stirred at 22° for 55 min. The reaction was diluted with ethyl acetate (50 ml) and was washed with 2N-hydrochloric acid and water then extracted with 5% sodium carbonate solution. The combined extracts were acidified with 2N-hydrochloric acid to pH 1 and extracted with ethyl acetate. The combined extracts were washed with water and saturated sodium chloride solution and dried and the solvent removed to give a colourless froth (0.522 g) which was crystallised from ethyl acetate to give the title ester as colourless prisms (0.307 g) mp 174° to 179°, $[\alpha]_D+107$ (c 1.0,dioxan).

EXAMPLE 9

9α-Fluoro-11β,17α-dihydroxy-16-methylene-3-oxoandrosta-1,4-diene-17β-carbothioic Acid.

A solution of 9α-fluoro-11β,17α-dihydroxy-16-methylene-3-oxoandrosta-1,4-diene-17β-carboxylic acid (0.218 g) in dry N,N-dimethylformamide (10 ml) at 22° under nitrogen was treated with N,N'-carbonyldiimidazole (0.254 g) and the reaction was stirred at 22° for 4 hrs. Hydrogen sulphide gas was bubbled into the reaction for 5 min and the mixture, now pale green, was stirred for 1 hr at 22°. The mixture was diluted with ethyl acetate (150 ml) and the solution was washed with 2N-hydrochloric acid, water and saturated sodium chloride solution, dried and the solvent removed in vacuo to give a yellow froth (0.222 g) which was crystallised twice from ethyl acetate to give the title carbothioic acid (0.078 g) as white prisms, decomposed at ca. 250° without melting, $[\alpha]hd D+117°$ (c 0.32, dioxan).

EXAMPLE 10

9α-Fluoro-11β,17α-dihydroxy-3-oxoandrosta-1,4-diene-17β-carbothioic acid

A solution of 9α-fluoro-11β,17α-dihydroxy-3-oxoandrosta-1,4-diene-17β-carboxylic acid (4.5 g) in dry N,N-dimethylformamide (100 ml) was stirred under nitrogen with N,N'-carbonyldiimidazole (4.04 g) at 22° C. for 4 h. Hydrogen sulphide was then passed through the solution for 30 min and then kept for a further 15 min. The mixture was poured into a mixture of 2N-hydrochloric acid (250 ml) and ice (ca 100 g) and the resulting precipitate was collected, washed with water and dried to give a white solid (4.56 g). A portion (120 mg) was recrystallised from ethanol to give the title thioacid as colourless crystals (70 mg), m.p. 222°–225°, $[\alpha]_D+116°$ (c 0.57, dioxan).

EXAMPLE 11

6α,9α-Difluoro-11β,17α-dihydroxy-16α-methyl-3-oxoandrosta-1,4-diene-17β-carbothioic acid A solution of 6α,9α-difluoro-11β,17α-dihydroxy-16α-methyl-3-oxoandrosta-1,4-diene-17β-carboxylic acid (12.0 g) in dry N,N-dimethylformamide (250 ml) was stirred and treated with N,N'-carbonyldiimidazole (9.94 g) under nitrogen at room temperature. After 4 h, hydrogen sulphide was passed through the solution for 0.5 h and the mixture was kept for a further 0.5 h. The reaction mixture was poured into 2N-hydrochloric acid (500 ml) containing ice (ca 250 g). The resulting precipitate was collected, washed with water and dried in vacuo to give the title thioacid as a white solid (11.47 g), m.p. 230°–232°, $[\alpha]_D+94°$ (c 0.91, dioxan).

EXAMPLE 12

17α-Acetoxy-6α,9α-difluoro-11β-hydroxy-16α-methyl-3-oxoandrosta-1,4-diene-17β-carbothioic acid A solution of 6α,9α-difluoro-11β,17α-dihydroxy-16α-methyl-3-oxoadrosta-1,4-diene-17β-carbothioic acid (1.625 g) and triethylamine (2.0 ml) in dichloromethane (75 ml) was stirred at ca 0° C., treated dropwise with acetyl chloride (1.275 ml), then stirred at this temperature for 1.25 h. The mixture was washed with 2N-sodium carbonate (50 ml), water, 2N-hydrochloric acid (50 ml), water (3×50 ml), brine (50 ml), then dried and evaporated to a white solid (1.91 g). This was dissolved in acetone (40 ml) and stirred with diethylamine (4 ml) at 27° C. for 45 min. The mixture was concentrated to ca 25 ml and poured into 2N-hydrochloric acid (100 ml) containing ice (ca 100 g): after being stirred the resulting precipitate was collected, washed with water and dried to give a solid (1.685 g). A portion (400 mg) was recrystallised from ethyl acetate to give the title 17α-acetate (280 mg), m.p. 175°–177°.

EXAMPLE 13

17α-Butyryloxy-6α,9α-difluoro-11β-hydroxy-16α-methyl-3-oxo-androsta-1,4-diene-17β-carbothioic acid Using a similar procedure to that described in Example 12, 6α,9α-difluoro-11β,17α-dihydroxy-16α-methyl-3-oxoandrosta-1,4-diene-17β-carbothioic acid (2.0 g) was converted, with butyryl chloride (1.5 ml) instead of acetyl chloride, to the title 17α-butyrate (2.08 g). A portion recrystallised from ethyl acetate had m.p. 155°–157°.

EXAMPLE 14

9α-Fluoro-11β-hydroxy-3-oxo-17α-propionyloxyandrosta-1,4-diene-17β-carbothioic acid Using a similar procedure to that described in Example 12, 9α-fluoro-11β,17α-dihydroxy-3-oxoandrosta-1,4-diene-17β-carbothioic acid (3.8 g) was converted, using propionyl chloride (3.9 ml) instead of acetyl chloride and after aminolysis of the intermediate with diethylamine 10.35 ml), into the title 17α-propionate 4.17 g). A portion (350 mg) recrystallised from ethyl acetate gave colourless crystals (165 mg), m.p. 135°–138°, [α]$_D$+72° (c 0.92, dioxan).

EXAMPLE 15

6α,9α-Difluoro-11β-hydroxy-16α-methyl-3-oxo-17α-propionyloxyandrosta-1,4-diene-17β-carbothioic acid A solution of 6α,9α-difluoro-11β,17α-dihydroxy-16α-methyl-3-oxoandrosta-1,4-diene-17β-carbothioic acid (5.0 g) and triethylamine (6.15 ml) in dichloromethane (140 ml) was cooled with ice-salt and treated dropwise with propionyl chloride (4.74 ml). The reation mixture was stirred further at ca 0° C. for 0.75 h then washed successively with 2N-sodium carbonate, water, 2N-hydrochloric acid, water and brine. After being dried, solvent was removed to give a white solid (6.35 g). This was redissolved in acetone (120 ml) and diethylamine (12.5 ml): after being stirred at room temperature for 1 h the volume was reduced to ca 75 ml. The solution was poured into 2N-hydrochloric acid (200 ml) containing ice (ca 300 g) and the resulting precipitate was collected, washed with water and dried in vacuo to a white solid (5.17 g) m.p. 152°–155°. Recrystallisation of a portion (400 mg) from ethyl acetate gave the analytically pure title thioacid 17α-propionate as colourless crystals (290 mg), m.p. 161°–164°, [α]$_D$−27° (c 0.95, dioxan).

Preparation 1

9α-Fluoro-17α-hydroxy-16β-methyl-3,11-dioxandrosta-1,4-diene-17β-carboxylic acid A stirred suspension of 9α-fluoro 17,21-dihydroxy-16β-methylpregna-1,4-diene-3,11,20, trione (4.842 g) in tetrahydrofuran (50 ml) was cooleo in ice and treated dropwise over 5 min. with a solution of periodic acid (4.255 g) in water (15 ml). The reaction was stirred at 22° for 2.25 hr, when most of the suspension had dissolved. The solvent was removed in vacuo, with periodic addition of water to maintain the original volume. The resulting precipitate was filtered off, washed with water and dried in air and in vacuo to give the title carboxylic acid as cream prisms (4.55 g) mp 270° to 272° (dec), [α]$_D$+1360° (c 1.04,dimethylsulphoxide).

Preparation 2

9α-Fluoro-11β,17α-dihydroxy-3-oxoandrosta-1,4-diene-17β-carboxylic acid

A suspension of 9α-fluoroprednisolone (10 g) in dry tetrahydrofuran (55 ml) was stirred and treated with a solution of periodic acid (9.0 g) in water (90 ml) and the mixture was stirred at 22° C. for 2 h. It was then poured into iced-water (ca 400 ml) and, after being stirred for 15 min., the solid product was collected, washed with water, and dried to give the title acid as a solid (9.42 g). A portion recrystallised from ethanol had m.p. 289°–293° [α]$_D$+66 (c 0.73, methanol).

We claim:

1. A process for the preparation of a compound of the formula:

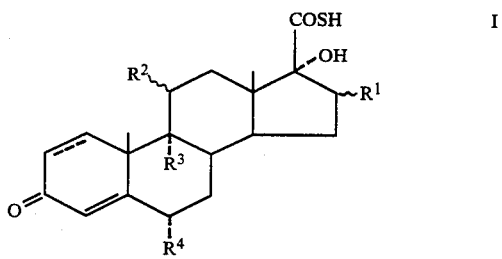

wherein

R$^1$ represents a hydrogen atom, a hydroxy group in the α-configuration, a methyl group which may be in either the α- or β-configuration or a methylene group;

R$^2$ represents a hydroxy or protected hydroxy group in either the α-or β-configuration or an oxo group;

R$^3$ represents a hydrogen, bromine, chlorine or fluorine atom; or R$^2$ and R$^3$ together represent a carbon-carbon bond or an epoxy group in the β-configuration;

R$^4$ represents a hydrogen or fluorine atom; and the symbol ==== represents a single or double bond; and the salts thereof, in which a compound of the formula:

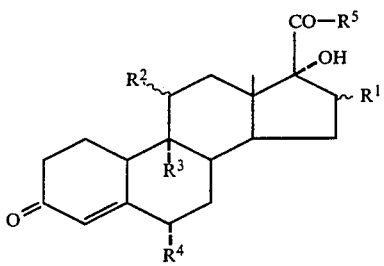

wherein
$R^1$, $R^2$, $R^3$ and $R^4$ are as defined above and $R^5$ represents a group of the formula:

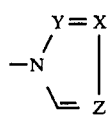

in which X, Y and Z, which may be the same or different, each represents CH or N, one or two of X, Y and Z being N, the heterocyclic ring optionally being substituted on at least one carbon atom by a lower alkyl group and/or where the heterocyclic ring contains two adjacent carbon atoms, the said ring optionally carrying a benzene ring fused to the said adjacent carbon atoms;
is reacted with hydrogen sulphide or a sulphide or hydrosulphide salt.

2. A process according to claim 1 wherein the compound of formula III is first prepared by reaction of a corresponding compound of formula III carrying a carboxylic acid group at the 17β-position with a symmetric or asymmetric compound of the formula:

$R^5-W-R^5$ 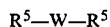 IV wherein W represents the group CO, CS, SO or $SO_2$ and the groups $R^5$, which may be the same or different, are as defined in claim 1.

3. A process according to claim 2 wherein a compound of formula IV is used in which W represents the group CO, CS or SO.

4. A process according to claim 3 wherein the compound of formula IV used is N,N'-carbonyldi(1,2,4-triazole), N,N'-carbonyldibenzotriazole, N,N'-carbonyldibenzimidazole, N,N'-carbonyldi(3,5-dimethylpyrazole) or N,N-thionyldiimidazole.

5. A process according to claim 3 wherein the compound of formula IV used is N,N'-carbonyldiimidazole or N,N'-thiocarbonyldiimidazole.

6. A process according to claim 2 wherein reaction of a compound corresponding to a compound of formula III, but carrying a 17β-carboxylic acid group with a compound of formula IV is followed in situ by reaction of the compound of formula III thus obtained, with hydrogen sulphide or a sulphide or hydrosulphide salt without isolation of the compound of formula III.

7. A process for the preparation of a compound of the formula:

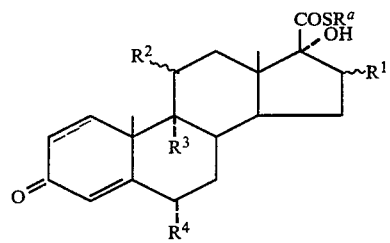

wherein
$R^1$, $R^2$, $R^3$ and $R^4$ are as defined in claim 1 and $R^a$ represents a $C_{1-6}$ alkyl group or a $C_{1-2}$ alkyl group carrying a terminal halogen atom or a benzyl group which may be substituted by a $C_{1-4}$ alkyl or $C_{1-4}$ alkoxy group or a halogen atom,
which process comprises esterifying the 17β-carbothioic acid group of a compound of formula I or a salt thereof.

8. A process according to claim 7, wherein $R^a$ represents a $C_{1-2}$ alkyl group carrying a terminal halogen atom.

* * * * *